United States Patent
Keusenkothen (10) Patent No.: US 9,963,641 B2
(45) Date of Patent: May 8, 2018

(54) METHOD OF FLUSHING PYROLYSIS REACTOR

(75) Inventor: Paul F. Keusenkothen, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 1083 days.

(21) Appl. No.: 14/116,366

(22) PCT Filed: Apr. 9, 2012

(86) PCT No.: PCT/US2012/032730
§ 371 (c)(1),
(2), (4) Date: Dec. 19, 2013

(87) PCT Pub. No.: WO2012/161872
PCT Pub. Date: Nov. 29, 2012

(65) Prior Publication Data
US 2014/0102874 A1    Apr. 17, 2014

Related U.S. Application Data

(60) Provisional application No. 61/490,489, filed on May 26, 2011.

(30) Foreign Application Priority Data

Aug. 18, 2011 (EP) ..................................... 11177896

(51) Int. Cl.
*B01J 8/04* (2006.01)
*C10B 43/08* (2006.01)
*B01J 19/00* (2006.01)
*B01J 19/24* (2006.01)
*C07C 2/76* (2006.01)

(52) U.S. Cl.
CPC ............. *C10B 43/08* (2013.01); *B01J 8/0492* (2013.01); *B01J 19/0026* (2013.01); *B01J 19/2485* (2013.01); *C07C 2/76* (2013.01); *B01J 2208/0053* (2013.01); *B01J 2219/00159* (2013.01); *B01J 2219/00247* (2013.01); *C10G 2300/301* (2013.01); *C10G 2300/708* (2013.01)

(58) Field of Classification Search
None
See application file for complete search history.

(56) References Cited

U.S. PATENT DOCUMENTS

| | | | |
|---|---|---|---|
| 1,880,308 A * | 10/1932 | Wulff | ........................ C07C 2/76 585/535 |
| 2,318,688 A | 5/1943 | Hasche et al. | |
| 2,319,679 A | 5/1943 | Hasche et al. | |
| 2,580,766 A | 1/1952 | Hall | |
| 2,629,753 A | 2/1953 | Frevel et al. | |
| 2,857,443 A | 10/1958 | Begley | |

(Continued)

FOREIGN PATENT DOCUMENTS

GB    1 165 870    10/1969

*Primary Examiner* — Jill Warden
*Assistant Examiner* — Dwayne K Handy (57) ABSTRACT

The present techniques provide a pyrolysis process that is reduced in coke and/or tar formation relative to comparable processes. A flushing fluid is applied or injected directly into a pyrolysis reactor to reduce high levels of coke and tar that can accumulate within the pyrolysis reactor during pyrolysis of the feed.

10 Claims, 3 Drawing Sheets

(56) References Cited

U.S. PATENT DOCUMENTS

| | | | |
|---|---|---|---|
| 3,786,110 A * | 1/1974 | Oleszko | B01D 51/10 208/48 Q |
| 2007/0191664 A1 | 8/2007 | Hershkowitz et al. | |
| 2008/0128330 A1 | 6/2008 | McCoy et al. | |
| 2009/0008292 A1 * | 1/2009 | Keusenkothen | C10G 9/26 208/81 |
| 2011/0291051 A1 * | 12/2011 | Hershkowitz | B01J 8/0492 422/198 |

* cited by examiner

METHOD OF FLUSHING PYROLYSIS REACTOR

PRIORITY CLAIM

This application is a national stage filing of International Patent Cooperation Treaty Application No. PCT/US2012/032730, filed Apr. 9, 2012, which claims priority from U.S. Ser. No. 61/490,489, filed May 26, 2011 and European Application No. 11177896.5, filed on Aug. 18, 2011, the disclosure of which is fully incorporated herein by reference.

BACKGROUND OF THE INVENTION

Pyrolysis is a thermal process in which hydrocarbons in a hydrocarbon stream are converted at an elevated temperature into lower molecular weight hydrocarbon molecules. Pyrolysis typically occurs at operating temperatures above 430° C. (800° F.). The term "pyrolysis" encompasses the decomposition of hydrocarbons in the presence of superheated water or steam (hydrous pyrolysis), for example, in the steam cracking of hydrocarbons.

Pyrolysis reactors have been used in refineries or chemical plants to produce different products from various hydrocarbon feeds for petrochemicals manufacture. For example, certain pyrolysis reactors are utilized to produce olefinic (e.g., alkenyl) materials. The feeds for this type of reactor typically range from ethane to vacuum gas oil, with heavier feeds giving higher yields of additional by-products, such as naphtha. As another example, pyrolysis reactors have also been used to produce alkynyl products, such as acetylene. The feeds for this type of reaction typically include methane.

As an example of the generation of alkynyl products, U.S. Pat. No. 2,319,679 describes one example of a pyrolysis system which may be used to produce acetylene containing product. The reactor in this system is a regenerative reactor or regenerative reverse-flow reactor in which heat is stored in refractory material for carrying out the pyrolysis of methane feed. During heating (e.g., regeneration), heat is supplied from the combustion of a fuel, with the hot combustion product flowing through the refractory material as a heat source. This heating is then stopped and methane is passed through the heated refractory material in an opposite direction of the flow of the combustion product. During pyrolysis, the methane is pyrolysed to form acetylene. The pyrolysis is then stopped and the flow of fuel is repeated to regenerate the reactor. The combustion of the fuel not only supplies heat for repetition of the pyrolysis, but results in burning of carbon materials that were deposited on the refractory walls during the pyrolysis.

As another example, U.S. Patent App. Pub. No. 2007/0191664 discloses a reverse-flow reactor in a pyrolysis system in which acetylene product is produced from a methane containing feed. The system includes a first and second reactor arranged in series to manage the flow of feed and product streams through the system. The reactors include multiple flow channels, such as channels in a honeycomb monolith arrangement, which provide increased efficiency and/or selectivity in producing acetylene product.

Because certain hydrocarbon feeds are more expensive than others, it is desirable to use lower cost, heavier hydrocarbon feeds in pyrolysis systems to produce olefins and acetylene products. However, the use of heavier feeds in pyrolysis systems tend to form higher amounts of coke and tar, which makes it more difficult to dispose of the heavier tar and coke by-products relative to lighter feed pyrolysis processes. This increase in coke and tar production is believed to result from the lower hydrogen content in the heavier feed.

Various other systems are able to utilize a quench fluid to quench the reaction and manage the production of coke with this fluid. As one example of a quench fluid, water has been used as a quench fluid in heavy oil pyrolysis processes. However, the water may result in the formation of emulsions that are difficult to manage in the process. Another example of is a quench fluid utilizes oil. Oil typically needs to be followed by a water quench to remove light condensable hydrocarbons from the stream, and the overall process is limited to a coke and tar production of up to about 30 weight percent (wt %).

Further, other regenerative processes may utilize a purging step to sweep the products out of the reactor. This step avoids contaminating products from one step with products from another step in the cyclical process. The purging step involves sweeping the purge fluid through the interior of the reactor to remove various vapor products. As an example, U.S. Pat. Nos. 2,629,753, 2,580,766 or 2,857,443 describe sweeping the reactor to remove the vapor products.

Other processes, such as steam cracking, may inject a fluid in equipment that is downstream of the steam cracking furnace when cracking heavy feeds. As an example, U.S. Patent App. Pub. No. 2008/0128330 describes a method of cleaning the downstream equipment from a furnace. In particular, the method involves the cleaning of a transfer line exchanger that is used to quench a steam cracking process. As the transfer line exchanger becomes coked and/or coated with a tar substance during the quenching step, a fluid is introduced into the transfer line exchanger to reduce the coke and tar build-up.

Because economics tend to further favor heavier feeds for pyrolysis processes, which result in increasing tar and coke formation, there is a need to develop improved pyrolysis processes that are more readily capable of handling a wider variety of hydrocarbon feeds than conventional pyrolysis processes for a regenerative reactor. There is also a desire of enhancing pyrolysis processes involving a regenerative reactor to increase the production of $C_2$ unsaturates (e.g., acetylene) in the pyrolyzed product, while also reducing the problems associated with coke and tar build-up. Moreover, there is also a desire to prolong the operation of the process and remove contaminates.

SUMMARY OF THE INVENTION

The present techniques involve a pyrolysis process. The pyrolysis process is carried out in such a manner that a wider variety of feeds may be more readily handled relative to conventional hydrocarbon processing schemes. The process further provides for a reduction in coke and tar formation.

According to one embodiment in accordance with the present techniques, there is provided a pyrolysis process that may be carried out in a regenerative pyrolysis reactor. The process includes a step of heating a stream in a preheat zone of the regenerative pyrolysis reactor. The heated stream is then reacted in a reaction zone of the pyrolysis reactor to produce a product. A flushing fluid is injected into the pyrolysis reactor to mix with the product downstream of the reaction zone, and the product is removed from the pyrolysis reactor.

The flushing fluid may be comprised of a polar fluid. For example, the flushing fluid may comprise steam or a polar aprotic fluid.

The process may further include a step of quenching the product in a quenching zone upstream of the injecting. Preferably, the product comprises acetylene.

The injecting step may be performed at locations within the reactor that have a peak pyrolysis gas temperature below 900° C., or below 600° C.

The process may additionally include a step of transferring heat to a material in a heat transfer zone downstream of the reaction zone and upstream of the injecting. Preferably, the product comprises carbon dioxide.

In an alternative embodiment, the process further comprises a step of heating a hydrocarbon stream in a second preheat zone of the regenerative pyrolysis reactor to produce a heated hydrocarbon stream. The heated hydrocarbon stream is then reacted in the reaction zone to produce a reactor product, with the reactor product being quenched in a quenching zone. A second flushing fluid may be mixed with the quenched reactor product, and the product removed from the pyrolysis reactor.

The process may also include a step of separating the flushing fluid from the product downstream of the regenerative reactor. The separated flushing fluid is preferably recycled to the reactor.

The process is particularly suited to pyrolysis of heavy hydrocarbon. For example, the stream being reacted may be comprised of a hydrocarbon having a nominal end boiling point of at least 400° F. (204° C.).

The flushing fluid is applied or injected directly into a pyrolysis reactor in an amount effective in reducing levels of coke and tar that are produced during pyrolysis of the feed. For example, the flushing fluid may be injected into the reactor at a weight ratio of flushing fluid to the produced product exiting the reaction zone of at least 0.0001:1, of at least 0.001:1, at least 0.01:1, or at least 0.1:1.

According to another embodiment, there is provided a system for processing hydrocarbons. The system is comprised of a regenerative pyrolysis reactor that includes one or more injection components at a first end; a reaction zone downstream of the one or more injection components; one or more removal components at a second end downstream of the reaction zone; and a flushing fluid line downstream of the reaction zone and upstream of the one or more removal components configured to inject flushing fluid at a reactor product exit location downstream of the reaction zone.

In one embodiment, the regenerative reactor comprises a first reactor bed and a second reactor bed coupled in series and disposed between the one or more injection components and the one or more removal components. Preferably, the reaction zone comprises a portion of at least one of the first reactor bed and the second reactor bed.

In an alternative arrangement, the regenerative reactor comprises one or more mixing components disposed between the first reactor bed and the second reactor bed. These beds may be configured to intermingle the streams within the reaction zone.

The system may also comprise a separator vessel downstream of the regenerative reactor, with the system configured to separate the flushing fluid from the remaining reactor product.

A water quench tower downstream may be included in the system downstream of the separator vessel and configured to contact the remaining reactor product with a water quench fluid to further cool the remaining reactor product.

The system may further include a transfer line exchanger downstream of the regenerative reactor and upstream of the separator vessel and configured to cool the reactor product flushing fluid. One or more lines may also be configured in the system in order to recycle the flushing fluid from the separator vessel to the regenerative reactor.

The flushing fluid line may be configured such that the line is comprised of a plurality of nozzles. The plurality of nozzles is optionally configured to distribute the flushing fluid to one or more removal components.

In an alternative arrangement, the flushing fluid line may comprise one or more lines disposed along an outer portion of an interior region of the regenerative reactor. The flushing fluid line may be comprised of one or more lines of lines coupled together to form a mesh to distribute the flushing fluid to the one or more removal components. The flushing fluid line may be disposed within or adjacent to the second reactor bed.

In yet another arrangement, the system may include a second flushing fluid line upstream of the reaction zone and downstream of the one or more injection components.

In an alternative embodiment, the regenerative reactor may further comprise one or more removal components at the first end; one or more injection components at the second end; and a second flushing fluid line downstream of the reaction zone and upstream of the one or more removal components.

BRIEF DESCRIPTION OF THE DRAWINGS

Examples of various preferred embodiments of this invention are shown in the attached Figures, wherein.

The invention will be described in connection with its preferred embodiments of the present techniques. However, to the extent that the following detailed description is specific to a particular embodiment or a particular use, this is intended to be illustrative only, and is not to be construed as limiting the scope of the invention. On the contrary, it is intended to cover all alternatives, modifications and equivalents that may be included within the spirit and scope of the invention, as defined by the appended claims.

DETAILED DESCRIPTION OF THE INVENTION

I. Use of a Flushing Fluid to Reduce Coke and Tar Levels

The present techniques involve a pyrolysis process, which may be carried out with reduced coke and/or tar formation relative to comparable processes. In this process, a flushing fluid is applied or injected directly into a pyrolysis reactor to reduce high levels of coke and tar that are produced during pyrolysis of the feed. Further, the use of the process may prolong the hydrocarbon processing operations of the system to reduce downtime (e.g., non-operational mode) and provide a mechanism to manage the processing of heavier hydrocarbon feeds.

The process of the present techniques is particularly suited to pyrolysis reactors that include a regenerative reactor or regenerative reverse-flow reactor. In particular, the regenerative reverse-flow reactor may have at least two reactor beds in fluid communication with each other and in series, one with the other. The present techniques may be particularly beneficial for pyrolysis processes that utilize a cyclical process that involves repeating a heating step, pyrolysis step and any other steps, if any, in each cycle. The flushing fluid is injected at a downstream location relative to the reaction zone, but within the reactor.

The process may include various steps during a hydrocarbon processing mode and a non-operational mode. The hydrocarbon processing mode may refer to the steps utilized by the reactor system to convert hydrocarbons into useful products, such as $C_2$ unsaturates. For instance, as noted above, the steps in a cyclical process may involve repeating a heating step, a pyrolysis step and any other steps, if any, in each cycle. Alternatively, a non-operation mode may be utilized for reactor cleaning operations. The non-operational mode is typically associated with downtime for a reactor, such as in the operation of a steam cracking furnace. It typically involves interrupting the flow of hydrocarbons to decoke the furnace, or reactor, where decoking refers to removal of at least a portion of coke deposited on various walls of the reactor system.

The process of the present techniques is particularly suited to pyrolysis reactors that operate a heating step (e.g., heating and regeneration) and a pyrolysis step (e.g., a reaction or pyrolysis) that is performed as part of the hydrocarbon processing mode. Such reactors may include, for example, a regenerative reactor and/or a regenerative reverse-flow reactor. For example, the flushing fluid may be injected along with the products (e.g., combustion products and/or reactor products) near the end of a step or may be injected as a separate step between the combustion and pyrolysis steps. Different aspects of the present techniques are explained further below.

II. Hydrocarbon Feed

The hydrocarbon feed used according to the present techniques can comprise any variety of hydrocarbon compounds. As used herein, the "hydrocarbon feed" contains hydrocarbons (C bound to H) and may contain (i) minor components of heteroatoms (<10 wt %) covalently bound to hydrocarbons and (ii) minor components of heteroatoms (<10 wt %) not bound to hydrocarbons (e.g., $H_2O$), wherein these weight percents are based on the weight of the hydrocarbon feed. Reference to "hydrocarbon compounds" or "hydrocarbons in the hydrocarbon feed" or "hydrocarbons of the hydrocarbon feed" means molecules within the hydrocarbon feed that contain at least hydrogen and carbon and, optionally containing heteroatoms such as oxygen, sulfur and nitrogen. Weight percents of hydrogen and carbon, as used to characterize the hydrocarbon feed, are typically provided as a percent of the hydrocarbons in the hydrocarbon feed. Preferably, the hydrocarbon compounds are comprised of at least 75 percent (%) of both carbon and hydrogen, based on total atom content of the hydrocarbon.

The hydrocarbon feed may include, by way of non-limiting examples, one or more of Fischer-Tropsch gases, methane, methane containing streams such as coal bed methane, biogas, associated gas, natural gas and mixtures or components thereof, steam cracked gas oil and residues, gas oils, heating oil, jet fuel, diesel, kerosene, gasoline, coker naphtha, steam cracked naphtha, catalytically cracked naphtha, hydrocrackate, reformate, raffinate reformate, Fischer-Tropsch liquids, natural gasoline, distillate, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, C4's/residue admixture, naphtha residue admixture, cracked feedstock, coker distillate streams, hydrocarbon streams derived from plant or animal matter and any mixtures thereof.

Particular hydrocarbons useful according to this invention are those that can be pyrolyzed to produce a product containing alkenyl containing compounds, alkynyl containing compounds or both. Particularly preferred are hydrocarbon compounds that can be pyrolyzed to produce product containing equal to or greater than (≥) 1 volume percent (vol. %), more preferably ≥3 vol. %, and most preferably ≥6 vol. % alkynyl containing compounds, based on total volume of pyrolyzed product produced form the pyrolysis process. The preferred alkynyl containing product comprises acetylene.

The term "pyrolysis feed" means the composition, which may be a mixture, subjected to pyrolysis. In one embodiment, the pyrolysis feed is derived from a hydrocarbon feed (e.g., by separation of a portion from the hydrocarbon feed and/or optional diluents). The diluent may be a composition that is used to control partial pressure in the vapor phase. Preferably, the diluent includes compounds that do not include any significant level of oxygen, because the presence of oxygen tends to produce undesirable levels of carbon oxides in the reactor product at the desired pyrolysis temperatures of the process. A preferred diluent is molecular hydrogen ($H_2$), particularly because hydrogen can also react with undesirable carbon by-products to reduce the formation of coke and tar-like by-products.

The pyrolysis feed is the hydrocarbon stream provided to the pyrolysis reactor (e.g., the stream that enters the pyrolysis reactor) and may contain one or more hydrocarbon feeds as well as a molecular hydrogen ($H_2$) containing feed. The pyrolysis feed may include hydrogen gas ($H_2$) in an amount that provides a preferred ratio of hydrogen gas ($H_2$) moles to the total moles of carbon (C) in the hydrocarbon components of the pyrolysis feed. The ratio of hydrogen to carbon ($H_2$/C) may be from 0.0 or 0.1 to 5.0, such as 0.0, 0.1, 1.0, 2.0, 3.0, 4.0, 5.0, or values in between. Combining the hydrogen content of the hydrogen gas to the hydrogen and carbon contents of the hydrocarbon components of the pyrolysis feed may result in a total atomic ratio of hydrogen (H) to carbon (C) in the pyrolysis feed that is in the range of 0.1 to 20 or in the range of 3 to 15. The weight percent of total hydrogen in the pyrolysis feed may be greater than that in the hydrocarbon feed. For example, the weight percent of total hydrogen in the pyrolysis feed may be from 8 wt % to 54 wt %.

The term "hydrogen content" means atomic hydrogen bound to carbon and/or heteroatoms covalently bound thereto and which excludes molecular hydrogen ($H_2$) in the hydrocarbon feed expressed as a weight percent based on the weight of the hydrocarbons in the hydrocarbon feed. Hydrogen content as applied to pyrolysis feed is expressed as an ASTM weight percent of hydrocarbons in the respective feed. As used herein, the expression "low hydrogen content feed" or "low hydrogen content hydrocarbon feed" means a feed with a hydrogen content of less than or equal to (≤) about 14 wt %. The hydrogen content of hydrocarbon feeds, reactants and products for present purposes can be measured using any suitable protocol (e.g., ASTM D4808-01 (2006), Standard Test Methods for Hydrogen Content of Light Distillates, Middle Distillates, Gas Oils, and Residua by Low-Resolution Nuclear Magnetic Resonance Spectroscopy or ASTM D5291-10 Standard Test Methods for Instrumental Determination of Carbon, Hydrogen, and Nitrogen in Petroleum Products and Lubricants).

Examples of the low hydrogen content hydrocarbon feeds include one or more of steam cracked gas oil and residues, gas oils, heating oil, diesel, gasoline, coker naphtha, steam cracked naphtha, catalytically cracked naphtha, reformate, raffinate reformate, distillate, crude oil, atmospheric pipestill bottoms, vacuum pipestill streams including bottoms, heavy non-virgin hydrocarbon streams from refineries, vacuum gas oil, heavy gas oil, atmospheric resid, heavy residuum and mixtures thereof. The low hydrogen content hydrocarbon feedstock may have a nominal end boiling point of at least 400° F. (204° C.), (e.g., ≥400° F., such as in excess of 1200° F. and even in excess of 1500° F.) and commonly has a nominal end boiling point of at least 500° F. (260° C.). Some preferred hydrocarbon feedstocks include crude oil, atmospheric and vacuum resids, tars, fuel oils and cycle oils. Such heavier, more aromatic feeds are typically lower cost, per unit weight, but may yield lower acetylene and ethylene yields and higher carbon or tar yields. Especially preferred feeds include aromatic feed, gas oils, cracked gas oils, crude, atmospheric resid feed, vacuum resid feed, tars, coal tars and heavy feed containing pitch. Due to the high aromatic content of the heavier feeds, the feeds have low hydrogen content (typically ≤about 11 wt % atomic hydrogen content). During pyrolysis, the hydrogen deficient feeds may form tar, coke, or soot.

III. Reactor

A reactor refers to equipment used for chemical conversion. As such, several items identified as reactors may be combined to become a single entity that is also identified as a reactor, in that individual and combined entities may be characterized as equipment used for chemical conversion.

A pyrolysis reactor refers to equipment for converting hydrocarbons by means of at least pyrolysis chemistry. The pyrolysis reactor may include one or more reactors and/or associated equipment and lines. That is, in certain embodiments, the pyrolysis reactor may include at least two reactors coupled in series and in fluid communication with each other, or may include two reactor beds in series within a single reactor. Examples of such reactors include, but are not limited to, regenerative reverse-flow reactors as described in U.S. Patent App. Pub. No. 2007/0191664; and pyrolysis reactors as described in U.S. Pat. No. 7,491,250, U.S. Patent App. Pub. Nos. 2007/0144940 and 2008/0142409.

Such a pyrolysis reactor involves at least pyrolysis chemistry. Pyrolysis or pyrolysis chemistry involves the conversion of hydrocarbons to unsaturates, such as ethylene and acetylene, which is an endothermic reaction requiring addition of heat. The terms "crack" and "cracking" may be used interchangeably with the terms pyrolyse and pyrolysis. In a pyrolysis reaction, ≥50%, ≥80%, or ≥90%, of this heat is provided by heat transfer via solid surfaces, such as tubulars or bed materials. Any combustion chemistry that occurs within the pyrolysis stream of a pyrolysis reactor provides a minority of the endothermic heat of pyrolysis, such as <50%, <20%, or <10% of the endothermic heat of pyrolysis.

A zone, as used herein, refers to a location within the pyrolysis reactor, which may include one or more reactors and/or associated equipment and lines. The zone may include a specific volume within a reactor, a specific volume between two reactors and/or the combination of different disjointed volumes in one or more reactors. The regenerative reverse-flow thermal pyrolysis reactors described herein may comprise first pyrolysis reactor and second pyrolysis reactor, for example as described in U.S. Patent App. Pub. No. 2007/0191664.

The reaction zone is a location in the pyrolysis system where greater than 50%, greater than 75% and/or greater than 90% of the conversion of hydrocarbons into $C_2$ unsaturates in the pyrolysis system is performed. That is, while some thermal cracking may occur upstream of reaction zone, the reaction zone is the location or volume within the reactor where a substantial amount of the smaller molecules are produced from the initial hydrocarbons provided to the reactor. For example, the reaction zone for a steam cracking system is in the radiant tubes of the steam cracking furnace, while the reaction zone is generally a central location between the reactor beds for a regenerative reverse-flow reactor, which may include a portion of the reactor beds near the central location and any mixing components disposed between the reactor beds.

In certain pyrolysis reactors (e.g., steam cracking furnace configuration), the heating and the pyrolysis process occur simultaneously, for example with a combusting stream on one side of partition (typically a wall or tubular) and the pyrolysis stream on the other side. Such reactors operate at or near steady state. The partition between the combustion feed and the pyrolysis feed has real physical dimensions and the temperature is not equal at every location. For example, on the combustion side, temperatures may be hottest near a flame region (e.g., burner), and on the pyrolysis side temperatures increase with heat addition until some maximum temperature is reached. Steady state in these systems means that, at any given location relative to the fixed partition, temperatures remain relatively steady. However, the gases that travel through the reactor are heated and cooled by the reactions and heat transfer that takes place in the reactor. The term "peak pyrolysis gas temperature" means the maximum temperature achieved by the bulk pyrolysis stream gases (e.g., portion of the pyrolysis stream passing through the reactor) as they travel through the pyrolysis reactor (e.g., reaction zone, such as the radiant section). One skilled in the art will appreciate that temperatures immediately proximate to the partition may be higher, and may, in some infinitesimal layer, actually approach the solid temperature. However, the pyrolysis temperature referred to herein should be considered a bulk gas temperature, which is a temperature that could be measured by a device (such as a thermocouple) that is not in contact with the solid material. For example, if the gas is traveling through tubulars in a thermal pyrolysis reactor, the bulk gas temperature may be taken as the average temperature over any tubular cross-section, and the peak pyrolysis gas temperature as the highest cross-sectional-average temperature of the pyrolysis stream.

Regenerative reverse-flow reactors may involve multiple steps repeated in sequence to form a cycle for the process. That is, the pyrolysis process may include two or more sequential steps, which include a heating step to heat the reaction zone and a pyrolysis step that converts the hydrocarbons into the reactor product. The steps may involve passing streams over a solid material in fixed orientation (e.g., one or more reactor beds), which utilizes valves to alternate introduction of hydrocarbon and/or combustion streams into the internal portion of the reactor. The solid material may be designed to facilitate the process of heat addition and removal. Checker bricks, tiles and monoliths may be used as the solid materials within the reactor. Such materials form a network of passages that are used by the gases in each step to transit the region containing solid material. The heat addition step leaves a profile of temperatures in the solid material, that is, a temperature that varies along the path by which the gases transit the solid material. The shape of that profile depends on many factors, including if and where a heat release (combustion) reaction occurs, the initial temperature distribution, the duration of the heating step, the flow rate and inlet temperature of the gas stream, and the heat capacity and transfer properties of the gas and solid material. On average, the solid material is hottest at the end of the heating step. The pyrolysis step consumes heat and reduces average solid material temperature. The pyrolysis step changes the profile of temperatures in the solid material, in a way that depends on many factors, including where the heat consumption (pyrolysis) reaction occurs, the initial temperature distribution, the duration of the pyrolysis step, the flow rate and inlet temperature of the gas stream, and the heat capacity and transfer properties of the gas and solid. Fixed-solid regenerative pyrolysis reactors do not operate in the steady state. That is, at any given location, the temperature changes. However, these reactors may be in a periodic steady state, meaning that the same cycling of temperatures occurs over and over as the reactor sequentially repeats the heating and pyrolysis steps.

The heat generated from the heating step may preferably be stored in a reactor bed or other solid material. The heat storing and transferring capacity of the material can be according to ΔTHT, which is defined as the ratio of bed-average volumetric heat transfer rate of the material to volumetric heat transfer coefficient of the material. Volumetric heat transfer rate is the product of the gas flow rate (e.g., gm/sec) across the material in a step, the heat capacity of the gas (e.g., ca./gm ° C.) and temperature change across the step (e.g. ° C.); the product quantity divided by the volume of the step (e.g., $cm^3$) traversed by the gas. In one embodiment, the solid material has a ΔTHT less than or equal to (≤) 500° C., ≤100° C., or ≤50° C.

Preferred heat storing and transferring material are materials that have relatively high volumetric heat transfer coefficient (e.g., ≥to 0.02 cal/$cm^3$ s ° C., preferably ≥about 0.05 cal/$cm^3$ s ° C., and most preferably ≥0.10 cal/$cm^3$ s ° C.), have low resistance to flow (low pressure drop), have operating temperature range consistent with the highest temperatures encountered during the heating step (e.g., regeneration and heating mode), have high resistance to thermal shock, and have high bulk heat capacity (e.g., at least about 0.10 cal/$cm^{3°}$ C., or preferably ≥about 0.20 cal/$cm^{3°}$ C.).

The heat storing and transferring material may be a ceramic, which may include yttria, ziconia, alumina, and/or other refractory material capable of withstanding temperatures within the pyrolysis reactor. In the present techniques, the pyrolysis reactor may operate at peak pyrolysis gas temperatures of at least 1200° C., at least 1700° C., at least 2000° C., preferably at least 1400° C., at least 1500° C., or more preferably at least 1540° C. That is, the peak pyrolysis gas temperature ranges may include temperatures from 1200° C. to 2200° C., from 1450° C. to 1700° C., from 1500° C. to 1675° C., or from 1540° C. to 1650° C. In some reactions, it may even be still more preferable to expose the pyrolysis stream to heat using very short residence times, such as ≤0.1 second, to a temperature in excess of 1600° C. When the pyrolysis feed comprises methane, pyrolysis reactions typically include peak pyrolysis gas temperatures in excess of 1400° C. for the methane to react or convert. An exemplary preferred process may pyrolyze the feed stream within the reactor, such as at peak pyrolysis gas temperatures of from 1540° C. to 2200° C., and more preferably from 1600° C. to 1800° C. Exemplary residence times preferably may be short, such as ≤0.5 second, ≤0.3 second and preferably ≤about 50 milliseconds or in the range of 0.5 seconds to 0.001 seconds.

In an embodiment, the reactor may include components comprised of yttria. In an embodiment, one or more of the reactor beds include separate conduits for separately channeling flow of feed components or regeneration fluid components (e.g., combustion stream components) through the reactor beds. Preferably, each reactor bed includes separate conduits. The separate flow channels in the reactor beds can further comprise flow barriers that effectively function as conduit walls to prevent cross flow or mixing of fluids between channels. Each reactor bed preferably includes multiple channels, which may preferably be in parallel flow arrangement.

In a particular embodiment, a channeled reactor bed may preferably be comprised of one or more honeycomb monoliths. Preferred honeycomb monoliths are structures that comprise many (e.g., a plurality, meaning more than one) gas flow passages or conduits, arranged in parallel fashion with walls serving to separate each passage or conduit. Such reactor can include a single monolith or a plurality of monoliths. Each monolith can be formed by extruding or die pressing monolith blocks with shaped (e.g., square or hexagonal) cross-section and two- or three-dimensionally stacking, such blocks above, behind, and beside each other. Monoliths are particularly effective as reactor beds because they provide high heat transfer capacity with minimum pressure drop.

Each monolith provides at least one flow channel (e.g., flow path) for respective streams used in the present techniques. Honeycomb monoliths can be further characterized as having open frontal area (or geometric void volume), such as from 20% to 80%, and having conduit density, such as from 50 to 2000 pores per square inch (pores/$in^2$), more preferably from 50 to 500 pores/$in^2$. The conduits may have a diameter of only a few millimeters, and preferably in the range of 0.5 millimeters (mm) to 10 mm.

Within the reaction zone, the components of the respective streams may intermingle from the separate channels within the reactor bed. That is, the mixing of the components may be performed in an open junction between reactor beds. In other embodiments, the reaction zone may include mixing components to enhance the blending or intermingling of the different components of the streams. Accordingly, a mixing component may be located between the reactor beds and configured to intermingle the components of the streams from at least one direction. The mixture is then passed downstream to the next or subsequent reactor component, such as another or second reactor bed. The mixing component is positioned between reactor beds so as to enhance mixing of combustion streams during the heating step. The mixing component is also positioned between reactor beds to enhance mixing and distribution of hydrocarbon feed and reactor product during the pyrolysis step.

IV. Heating Step

As noted above, the present techniques differ in at least one particular way from conventional steam cracking processes to the extent that this pyrolysis process may include one or more steps in a cycle during hydrocarbon processing mode. One step can be referred to as a heating step (e.g., involving heating and regenerating). Another step can be referred to as the pyrolysis step (e.g., pyrolysis or hydrocarbon conversion mode). These different steps may be performed in sequence to form a cycle, which is then repeated as part of the normal hydrocarbon processing operations. The cycle may be performed continuously, semi-continuously, periodically or even as a batch operation. Accordingly, a cycle includes the time spent in heating step plus time spent in pyrolysis step plus any time needed to switch between steps or for additional steps before the repeat of the sequence. Typical cycle times may be in the range of 1 to 240 seconds, or in the range of 2 to 60 seconds. The heating and pyrolysis steps may have equal durations or may be adjusted to have different durations.

In the heating step, combustion feeds are supplied to or injected into a first reactor end zone (e.g., at or adjacent to a first end of a first reactor bed). That is, one or more combustion streams flow through a first reactor end zone, which may be a portion of the first reactor bed and the first interior region of the reactor upstream of the first reactor bed and downstream of the combustion injection components, or only the first interior region (along the flow of the combustion stream). The combustion streams may flow through conduits through a combustion preheat zone (e.g., a portion of the first reactor bed) to the reaction zone, where the combustion streams exothermically react to heat the reaction zone. In another embodiment, one combustion stream may flow through the reactor and the other may be supplied directly to the reaction zone. Preferably, the combustion streams may include a fuel stream and an oxidant stream that are maintained substantially separate until passing to the reaction zone and are capable of reacting together and combusting to supply or generate heat and produce combustion products.

The combustion streams may include two or more individual feeds that are to be combined to form a combustion reaction or a mixture of the two or more feeds, such as a fuel that does not contain oxidants (e.g., $O_2$) or non-combustible non-volatiles and a combustion oxidant that may include an oxygen or oxygen containing fluid. The fuel stream may be a hydrogen-containing composition of hydrogen, hydrocarbon or a mixture thereof. The hydrocarbon can be the same or different from the hydrocarbon used in the feed. Additional or further specific examples of fuel compositions that can be used include, but are not limited to, hydrogen, methane, ethane, ethylene, propane, propene, butane, butene, hexane, heptane, methanol, ethanol, propanol, butanol, dimethyl ether, diethyl ether, liquid natural gas (LNG), liquid petroleum gas (LPG), naphtha, gasoline, kerosene, light gas oil, heavy-oil decomposition components having a final ASTM D 86 boiling point of not greater than 565° C., natural gas, coal bed methane, landfill gas, blast furnace gas, coke oven gas, converter gas, by-product gas derived from a chemical plant, gas obtained by gasification of coal or heavy oil, coal carbonization gas, water gas from the gasification of coal, coal partial-combustion gas, light oil or gas obtained by thermal separation of heavy oil, heavy-oil thermal decomposition light-oil or gas, heavy-oil oxidation decomposition light-oil or gas, super-heavy oil thermal decomposition light-oil or gas, super-heavy oil oxidation decomposition light-oil or gas, fermentation gas, including mixtures of one or more of these substances.

The oxidant stream may include an oxygen composition that has sufficient oxygen content to enable the fuel to combust. Oxidant can be supplied in any form suitable for combustion, such as pure oxygen or in the form of air. The oxidant stream may include, but is not limited to, air, oxygen or mixtures thereof. Any of the fuel or oxidant may additionally include non-combustible but volatile diluents such as $N_2$, $CO_2$, $H_2O$, and/or other inert gases. In an embodiment, the combustion oxidant comprises oxygen in an amount of at least 80% of stoichiometric for complete combustion of combustion fuel composition. Preferably, the combustion oxidant comprises oxygen in a stoichiometric amount for complete combustion, and more preferably in an amount in excess of stoichiometric for complete combustion of the combustion fuel composition in the combustion streams.

The fuel and the oxidant are preferably not mixed until the reaction zone. That is, the combustion streams are flowed to the reaction zone through the combustion preheat zone in separate channels (e.g., a portion of a first reactor bed). For example, the fuel and oxidant can be separately flowed through separate channels of a honeycomb channel arrangement of a first reactor bed. The fuel and oxidant are preferably heated as they flow through the channels. Following heating, the fuel and oxidant are then preferably mixed, with combustion taking place.

At a point downstream of the combustion preheat zone (e.g., the reaction zone), the streams are mixed together to exothermically react to produce combustion products and heat. Preferably, the fuel and oxidant components are mixed together in the mixing component within the pyrolysis reactor. The combustion streams flow through the combustion preheat zone and exit into the reaction zone (e.g., a portion of the first reactor bed, a portion of second reactor bed and one or more mixing components, if any), where the fuel and oxidant components are mixed together and combusted to produce combustion products and heat. Heat is generated from the exothermic reaction of the fuel and oxidant components, which is carried along with the downstream flow of combustion products or materials.

The combustion products are then flowed downstream to a combustion heat transfer zone (e.g., a portion of the second reactor bed) with the combustion heat transfer zone absorbing heat produced from the combustion of the combustion streams. The heat is absorbed by the heat storing and transferring material, noted above, which may be include at least a portion of the second reactor bed. This absorbed heat by the material in the combustion heat transfer zone is sufficient to enable pyrolysis of the hydrocarbon stream (e.g., hydrocarbons in the pyrolysis feed) that flow through the pyrolysis preheat zone (e.g., a portion of the second reactor bed) in the pyrolysis step, which is discussed further below. The heat may also be sufficient to enable coke or tar components that may have accumulated in the combustion heat transfer zone during a previous pyrolysis step to be burned, thereby regenerating the combustion heat transfer zone.

Then, the combustion products flow through the second reactor end zone, which may be a portion of the second reactor bed and a second interior region of the reactor downstream of the second reactor bed and upstream of the combustion removal components, or just the second interior region. This heating and regeneration of the heating step is particularly beneficial in a cyclic process that incorporates both the heating step and the pyrolysis step.

V. Pyrolysis Step

In the pyrolysis step, pyrolysis feed comprising hydrocarbon, and optionally diluents such as molecular hydrogen ($H_2$), is supplied to or injected into another end of the reactor via pyrolysis injection components. The pyrolysis feed may be supplied to or injected into the pyrolysis reactor following the removal of the combustion products from the heating step. In addition, a sweeping or purging step may be included to remove products (e.g., gaseous components) from the internal regions of the entire reactor. That is, the pyrolysis stream flows through the second reactor end zone, which may be a portion of the second reactor bed and the second interior region of the reactor upstream of the second reactor bed and downstream of the pyrolysis injection components, or only the second interior region (along the pyrolysis stream's flow). This pyrolysis or hydrocarbon stream may be provided at a different end of the reactor from the end that the combustion streams were supplied or injected. The direction of flow of the pyrolysis stream may be counter to the direction of flow of the combustion streams, or in certain embodiments may be in the same direction, which may also involve some alternating patterns of flow. Based on the example above in which the reactor includes at least two separate reactor beds in series, the pyrolysis stream is flowed into a pyrolysis preheat zone (e.g., a portion of the second reactor bed) from the second reactor end zone. For instance, the hydrocarbon stream may flow through conduits or channels in a through the second reactor bed, such as a honeycomb channel arrangement, as described above.

As the hydrocarbon stream flows through the pyrolysis preheat zone, the temperature along the path of flow increases. As the temperature increases to the appropriate level, pyrolysis of the hydrocarbon in the hydrocarbon stream takes place in a reaction zone (e.g., a portion of the first reactor bed, a portion of second reactor bed and one or more mixing components, if any). Following the reaction zone, the reactor products (e.g., unreacted and reacted hydrocarbons) are flowed through a pyrolysis quenching zone (e.g., a portion of the first reactor bed), which reduces the temperature of the reactor products. The reactor products may flow through channels in the first reactor bed. The reactor products are then removed from the pyrolysis quenching zone to the first reactor end zone, and further passed for processing in recovery units to process and separate one or more of acetylene, ethylene and hydrogen.

In this pyrolysis step, the pyrolysis reaction is carried out relatively quickly to avoid over-cracking so as to avoid excessive formation of undesirable by-products, particularly coke and tar compositions. Accordingly, pyrolysis reactors may be characterized in terms of the residence time of pyrolysis gases in the reactor. Residence time is considered to be the total time from the hydrocarbon entry into the pyrolysis reactor and the corresponding exit of the reactor product from the reactor. Residence time is most generally defined as the time required for some average non-reacting molecule to pass through the pyrolysis reactor or furnace. Residence time may be further defined to be the time spent within the actively heated or cooled portions of the reactor or furnace. This includes time spent within tubulars or heat transfer solids of a furnace or regenerative reactor, respectively, but excludes residence time spent in headers or other means of conveyance to or from the actively heated or cooled regions of the furnace or reactor. An exact calculation of residence time requires measurements with tracer compounds (such as radioactive additives to the feed) or requires a specific knowledge of the temperature and composition of the pyrolysis stream at all times as it passes through the pyrolysis reactor. For the purposes of the present techniques, residence time (in either form) may be approximated using interpolation and extrapolation of discreet composition and temperature measurements, and/or using model-based estimations of temperature and composition, as is known in the art. As an example, the residence time for a regenerative reverse-flow reactor is the time from the injection of the pyrolysis feed via the pyrolysis injection component, time traveling through a second reactor bed and a first reactor bed and the time to enter into the pyrolysis removal component. As noted above, residence times may be ≤0.5 second, ≤0.3 second and preferably ≤about 50 milliseconds or in the range of 0.001 to 1.0 seconds or in the range of 0.5 seconds to 0.001 seconds.

Further, different types of thermal pyrolysis reactors may have different heat profiles. That is, some embodiments of pyrolysis reactors may operate in an isothermal manner with the heat profile being relatively constant. However, other pyrolysis reactors may have a heat profile that is similar to a Gaussian curve. As an example, a regenerative reactor may be characterized by an initial and final temperature of 300° C. and a peak pyrolysis gas temperature of 1700° C. over at a residence time of 35 ms (≤10 ms at temperatures ≥1000° C.).

Pyrolysis of the hydrocarbons in the pyrolysis feed may involve different operating conditions, such as temperatures and pressures. The temperatures may involve those noted above. Similarly, the pressure within the reactor can vary from vacuum conditions to higher pressures. For example, pressure within the reactor may be ≥4 psig (27 kPa), ≥15 psig (103 kPa), ≥36 psig (248 kPa), ≥44 psig (303 kPa) or ≥103 psig (710 kPa), but may be ≤300 psig (2068 kPa), ≤163 psig (1124 kPa), or ≤150 psig (1034 kPa). As may be appreciated, these different pressures may be combined together to form different combinations depending on the specific configuration of equipment. In some embodiments, the process conditions may be at a vacuum pressure, such as ≤15 psia (103 kPa).

The quenching zone may include a portion of the first reactor bed, where the endothermic reactions are slowed. That is, average temperature within the quenching zone is less than the average temperature in the reaction zone, such as at least 50° C. or at least 100° C. or at least 200° C. less than the average temperature in the reaction zone. This quenching zone may include gas temperatures equal to or below 1274° C., and temperatures equal to or above (≥) 400° C., ≥600° C., or ≥750° C. In the quenching zone, the rate of reactions that produce acetylene may be lowered and other reactions that form carbon and other hydrocarbon compounds may also be reduced. Quenching is generally a rapid cooling that involves passing the reactor products through the reactor bed. That is, due to heat transfer with the solids and endothermic cooling, rates of reactions (e.g., formation of acetylene and coke) are slowed.

The quenching zone may be characterized by pyrolysis gas temperatures that comprise reduced rates of acetylene formation relative to the reaction zone. As an example, the process may include the thermal conversion of methane at a pressure of 14.7 psig (101 kPa) and with 2:1 molar ratio of hydrogen diluent. At temperatures at or above 1274° C., yields of acetylene can exceed 10 wt % of the starting methane, at some time ≤0.1 seconds, which may be part of the reaction zone. Conversely, at temperatures below 1274° C., there are no times ≤0.1 seconds for which yields of acetylene reaches 10 wt % of the starting methane, which may be characterized as part of the quench zone.

In certain embodiments, the quenching zone may be actively performed by injecting water, other hydrocarbon oils, solvent or other suitable fluids into reactor end zone As may be appreciated, the flow of hydrocarbons is interrupted after a desired or predetermined time, reactor products are removed and the combustion feeds are provided to again heat the reactor. By repeating the heating step and the pyrolysis step, the overall reaction process can be continuously carried out over a relatively long period of time.

VI. Flushing Fluid

A flushing fluid is provided or injected into the pyrolysis reactor as a separate step or during a portion of the pyrolysis step and/or heating step. The flushing fluid may be added to the product (e.g., reactor product or combustion product) downstream of the reaction zone relative to the flow of the respective product. In particular, the flushing fluid may be provided at a location in the first reactor end zone or second reactor end zone prior to the product exiting the reactor via removal components. For example, the flushing fluid may be provided downstream of the quenching zone or at an upstream location in the quenching zone where coke may deposit on the reactor bed near the pyrolysis removal components. This flushing fluid acts to displace or remove compositions (e.g., carbon material) that were formed during the pyrolysis step, particularly material deposited on channel walls of the reactor or at the pyrolysis removal components of the pyrolysis reactor, including valves or other structure that control the exit of the reactor product from the reactor. Further, while the flushing fluid may be provided in the reactor end zone, the flushing fluid may also act as a cooling fluid to further cool the reactor product within the reactor after it has been quenched to substantially reduce the further reactions of the reactor products (e.g., acetylene) into undesired products (e.g., coke). By cooling the reaction at the desired level, the formation of undesirable by-products can also be reduced.

Preferred flushing fluids are fluids that convey coke away with the flushing fluid, and/or the solubilize coke. Such fluids are preferably polar aprotic fluids and steam. Polar aromatic fluids are those that have a large dipole moment, high dielectric constant, aromatic or a combination thereof.

In an embodiment, the flushing fluid has a dipole moment of at least 1.5 debye (D), preferably at least 1.6 D, and more preferably at least 1.8 D. In an alternate embodiment, the flushing fluid has a dielectric constant (k) of at least 5, preferably at least 6, more preferably at least 7. In another alternate embodiment, the flushing fluid may have a miscibility in water of at least 10 grams of fluid per 100 grams of water, preferably at least 15 grams of fluid per 100 grams of water, and more preferably at least 20 grams of fluid per 100 grams of water. Dipole moments for a solvent may be found in the *CRC Handbook of Chemistry and Physics* (65th ed.), CRC Press, or may be determined by measuring the capacitance with a dipole meter. Each of the measurements indicated are measurements under standard temperature and pressure conditions, e.g., 20° C. and 1 atmosphere.

The flushing fluid can be a polar protic or polar aprotic fluid. These polar protic and aprotic fluids are fluids that have a relative static permittivity greater than 15. Protic fluids refer to compounds that have a hydrogen atom bound to an oxygen (as in a hydroxyl group) or a nitrogen (as in an amine group) atom. More generally, any compound that contains dissociable proton(s) (H+), or that can donate a proton (H+), is referred to as a protic fluid. Conversely, aprotic fluids cannot donate hydrogen. Polar protic fluids are, therefore, fluids that share ion dissolving power with aprotic fluids but have an acidic hydrogen. Examples of polar protic fluids include, but are not limited to, formic acid, butanol, isopropanol, n-propanol, ethanol, methanol, acetic acid and water. Aprotic fluids refer to compounds that do not contain dissociable proton(s) (H+), or that do not donate a proton (H+), but have a large dipole moment, such as at least 1.5 D. In one aspect, this large dipole moment is generated by a multiple bond between carbon and either oxygen or nitrogen. The protic fluids are dipolar aprotic fluids that contain a carbon-oxygen double bond. Examples of aprotic fluids include, but are not limited to, dichloromethane, tetrahydrofuran, ethyl acetate, acetone, dimethylformamide, acetonitrile, and dimethyl sulfoxide.

The flushing fluid may include a mixture of different compounds. In such a mixture, every compound in the mixture may not individually meet the desired characteristics of polarity, such as dipole moment, dielectric constant, and miscibility with water. However, in the case that the flushing fluid is comprised of a mixture of compounds, the overall mixture should exhibit the desired polarity characteristics. For example, the mixture of components should exhibit the desired characteristics of one or more desired dipole moment, dielectric constant, and miscibility with water.

In an embodiment, flushing fluids having a boiling point at 1 atmosphere of ≥100° C., or ≥200° C., ≥300° C., ≥400° C. or ≥500° C. can be effectively used, but may be 600° C. If the flushing fluid comprises a mixture of compounds, higher boiling point fluids may be preferred, with the boiling point in mixtures referring to final boiling point as determined by testing method ASTM D 86.

The flushing fluid may be provided at various locations within the reactor, which are downstream of the reaction zone. For example, in one embodiment, the flushing fluid is injected into the pyrolysis reactor at an end of the first reactor bed near the pyrolysis removal components and/or at an end of the second reactor bed near the combustion removal components, with downstream referring to the direction of flow of reactor product or combustion product during the respective step. The flushing fluid may be injected via a sparger disposed between a reactor bed and the removal components in the reactor end zone, injected into a fluid distribution component disposed within the reactor bed or integrated into the reactor bed at a location downstream of the reaction zone and upstream of removal components, and/or at any suitable location in the pyrolysis reactor downstream of the quenching zone/combustion heat transfer zone and upstream of the exit of the respective product from the pyrolysis reactor.

The flushing fluid is applied or injected directly into a pyrolysis reactor in an amount effective in reducing levels of coke and tar that are produced during pyrolysis of the feed. The flushing fluid may be injected during the pyrolysis step, during the heating step, as a separate step, or during each of the steps. If the flushing fluid is injected during the pyrolysis step and/or the heating step, the flushing fluid may be injected for a set period of time during the step or may involve injecting a certain amount of flushing fluid for the respective step. This may be done on a semi-continuous basis or even a periodic basis. Accordingly, the flushing fluid can be injected into the reactor during pyrolysis step at a weight ratio of flushing fluid to overall reactor product exiting the reaction zone of at least at least 0.0001:1, of at least 0.001:1, at least 0.01:1, at least 0.1:1, or at least 1:1, for different embodiments.

For example, if the flushing fluid is injected during at least a portion of the pyrolysis step, the flushing fluid can be injected into the reactor during pyrolysis step of the cycle at a weight ratio of flushing fluid to overall reactor product exiting the reaction zone of at least 0.001:1 or at least 0.01:1. In certain embodiments, it is preferred that flushing fluid be injected into the reactor at a weight ratio of flushing fluid to overall reactor product exiting the reaction zone of not greater than 0.1:1 or not greater than 0.05:1. Further, the flushing fluid may be injected for a certain period of time, which may be in the range of 10% to 35% of the time allocated for the step (e.g., the latter or end of the step).

As another example, if the flushing fluid is injected on a periodic basis, it may be injected during the pyrolysis step, during the combustion step or after the pyrolysis or combustion step. The period may involve every other cycle, every third cycle, every fourth cycle, or any other suitable period. In certain embodiments, it may involve injecting the flushing fluid once the pressure changes within the reactor, or removal components are determined to require cleaning. The flushing fluid can be injected into the reactor during the cycle at a weight ratio of flushing fluid to overall reactor product exiting the reaction zone of at least 0.1:1 or at least 1:1. Further, the flushing fluid may be injected for a certain period of time, which may be every hour of operation, once a day for a certain number of cycles or other time periods.

The exit of reactor product from the reactor can be controlled by any appropriate pyrolysis removal components, such as by appropriate arrangement of valves and manifolds, which may include a poppet valve configuration, such as in U.S. Patent Ser. No. 61/349,464, which is incorporated herein. The use of flushing fluid according to the present techniques effectively enhances the removal of coke or tar-like material from collecting not only in the pyrolysis removal components, but may also be utilized to remove coke or tar-like material from a portion of the reactor bed near the pyrolysis removal components. Thus, a significant portion of coke and/or tar material may be removed from the pyrolysis reactor through appropriate application of the flushing fluid.

Selection of the flushing fluid may depend on the specific configuration and feed being processed. For example, in the heating step, the flushing fluid may include steam. The steam is easy to separate from the combustion products and may be recycled to the process or utilized in other processes depending on its pressure and temperature. Similarly, the flushing fluid for the pyrolysis step may include steam and/or a hydrocarbon (e.g., heavy hydrocarbons and/or heavy aromatics). The hydrocarbon and/or steam as a flushing fluid do not introduce additional contaminates into the processing of the reactor products and are easy to separate from the lighter reactor products in recovery processes. Other specific flushing fluids may be utilized as noted further below.

VII. Reactor Product Processing

The reactor product may contain the desired pyrolysis compounds, such as the desired alkenyl compounds, alkynyl compounds or both, but the pyrolyzed product also includes removed coke and tar material, as well as some amount of a wide variety of lighter and heavier boiling co-products. To recover the more desired compounds in the reactor product, the reactor product is removed from the pyrolysis reactor as an effluent stream, and the effluent stream is separated into various components, such as according to relative boiling point ranges. Any appropriate equipment can be used in this separation, such as evaporators, flash drums or any variety of distillation equipment or columns. In one exemplary configuration, the effluent stream (e.g., reactor product leaving the reactor) may be provided from the pyrolysis reactor to a heat exchanger to further cool the effluent stream and recover heat from the effluent stream. Then, the effluent stream may be provided to a solid removal unit to remove solids, such as coke, and/or other materials, such as tar from the reactor effluent. The remaining effluent stream may then be subjected to various separation processes to remove light gases, such as hydrogen and methane, and/or to remove heavy products. Then, the remaining effluent stream may be provided to an acetylene converter unit to convert at least a portion of the acetylene into ethylene. In other embodiments, the effluent may be further processed into polyethylene or polypropylene in additional processing units.

In addition to the typical separations, the recovery units may also be configured to recover, regenerate and recycle the flushing fluid from the other reactor products in the effluent stream. As an example, this may include additional units or may involve the existing downstream units with additional recycle streams. For instance, if steam is the flushing fluid, it may be removed as part of a water quench tower (e.g., utilized for cooling the effluent and/or solid removal), or other separation processes. If heavy hydrocarbons are utilized as the flushing fluid, then a liquid vapor separator vessel may be utilized to separate the heavy hydrocarbons from the lighter hydrocarbons that are to be further processed into other products.

In another embodiment, the effluent stream is further cooled downstream of the pyrolysis reactor to form a first cooled stream comprised of a first condensed fluid and a first non-condensed fluid. The first cooled stream can then be sent to a first separator vessel to separate the first condensed fluid from the first non-condensed fluid. To reduce or minimize fouling of equipment at this step of processing, the first non-condensed fluid that is separated at the first separator vessel can be contacted with a water quench fluid to further cool the first non-condensed fluid. This further cooling produces a second cooled stream comprised of a second condensed fluid and a second non-condensed fluid. The second cooled stream is sent to a second separator vessel to separate the second condensed fluid from second non-condensed fluid.

VIII. Exemplary Embodiments

Figure 1:
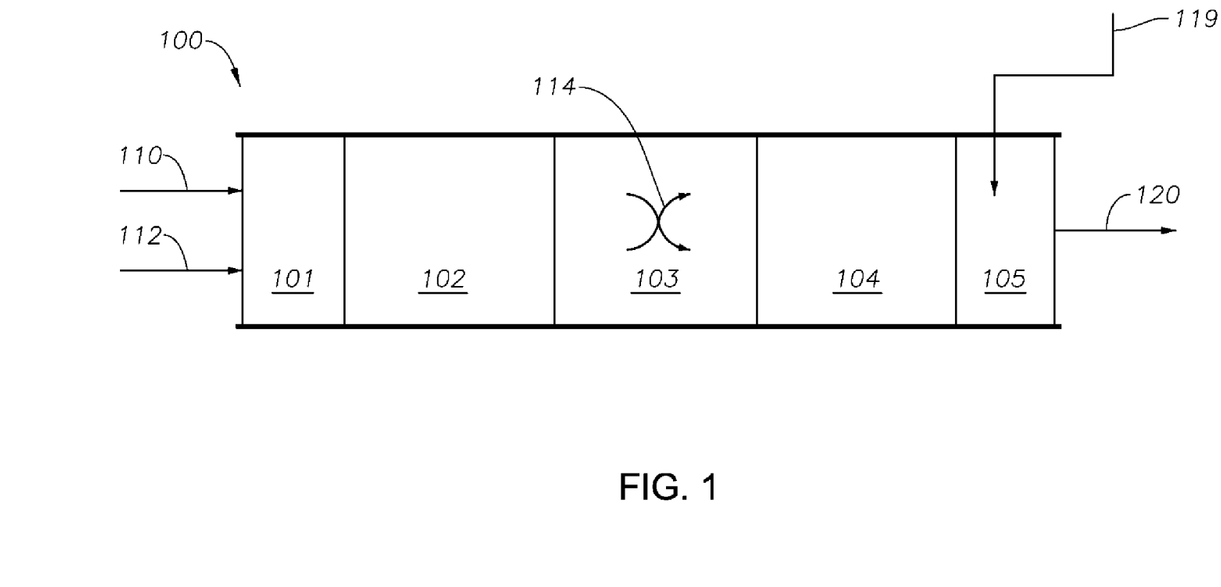
FIG. 1 is a flow diagram of heating step of a pyrolysis process in accordance with an exemplary embodiment of the present techniques.
Figure 2:
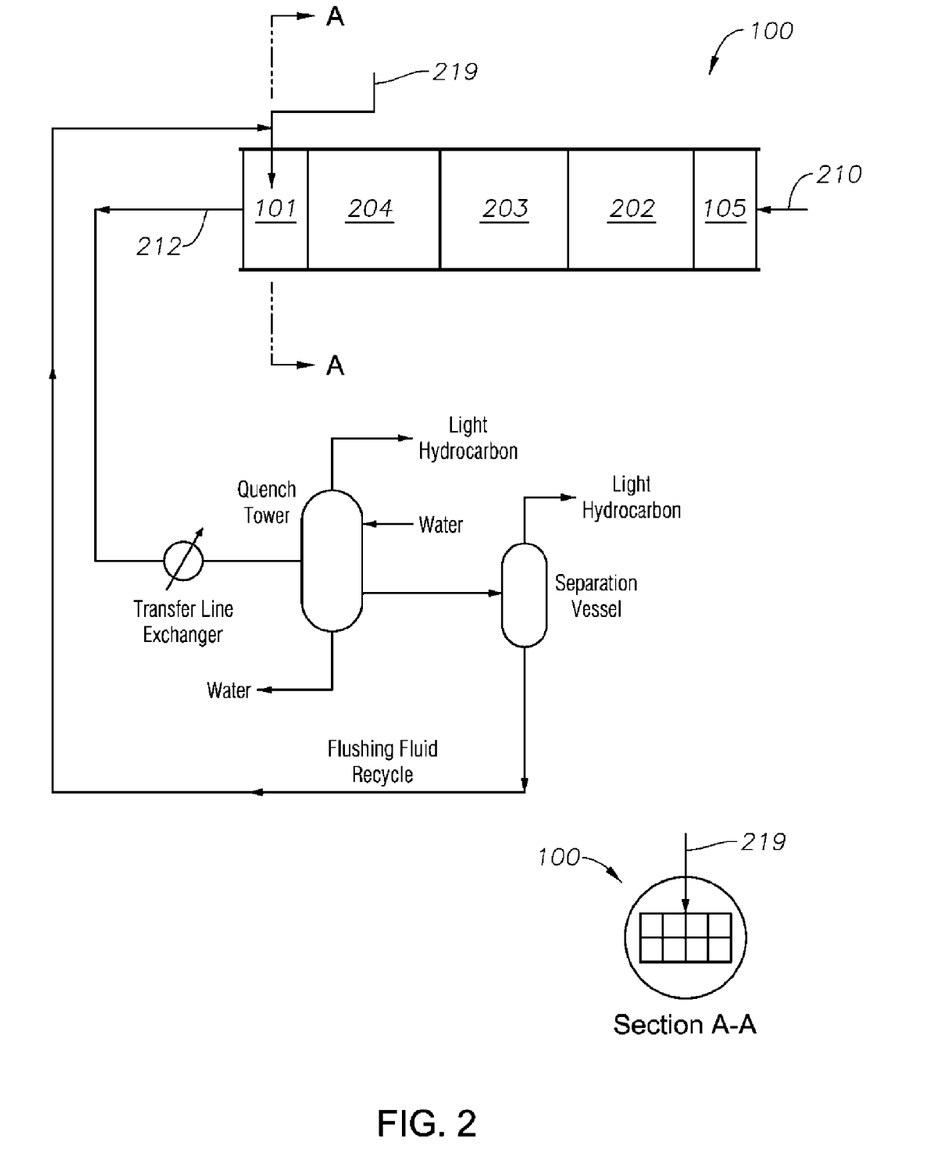
FIG. 2 is a flow diagram of the pyrolysis step of a pyrolysis process in accordance with an exemplary embodiment of the present techniques.
Figure 3:
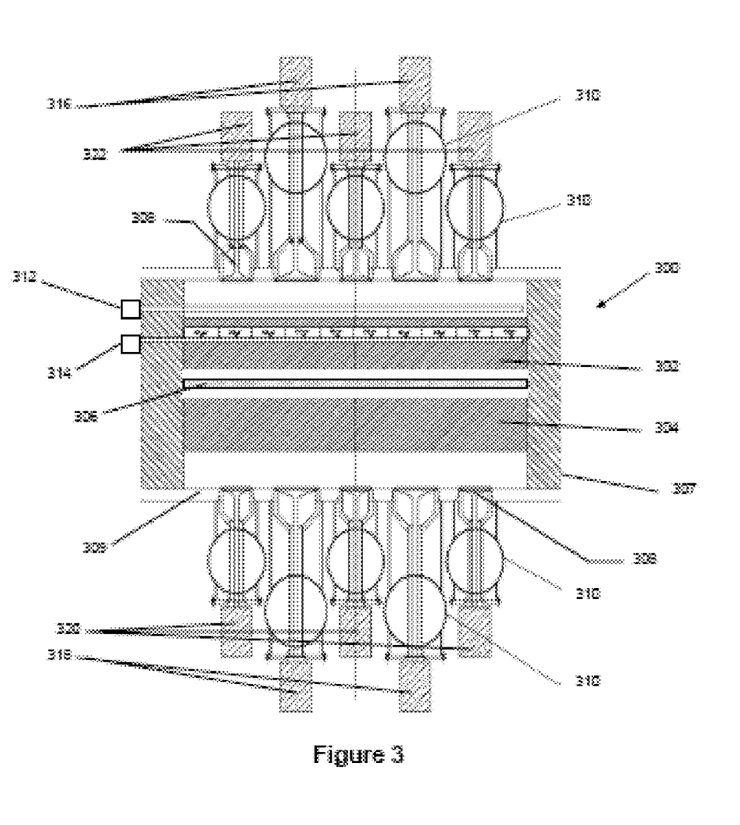
FIG. 3 is a diagram of an exemplary embodiment of a pyrolysis reactor in accordance with an exemplary embodiment of the present techniques.

An example of the process of the present techniques is demonstrated according to the schematics or process flow diagrams shown in FIGS. 1 to 3. The example is representative of a process that can be used in a regenerative type or a reverse-flow regenerative type of pyrolysis reactor.

FIG. 1 shows an example of the heating step that is carried out in accordance to an embodiment of the present techniques. According to FIG. 1, combustion streams, which includes a fuel stream 110 and an oxidant stream 112 are flowed to a first reactor end 101 and then to a first preheat zone 102 of pyrolysis reactor 100. These streams flow separately, through separate channels, such as honeycomb channels within the reactor 100. In one embodiment, the first reactor end zone 101 may include an internal region downstream of the combustion stream injection components within the reactor 100 and the first preheat zone 102 may include a portion of a first reactor bed downstream of the first reactor end zone 101. As the separate combustion streams flow in a downstream direction and exit the first preheat zone 102, the streams are mixed in the reaction zone 103, which may include mixing components, as shown by arrows 114. Combustion takes place in the reaction zone 103, with flow of the combustion products and any unreacted or uncombusted material in the combustion streams continuing downstream to a combustion heat transfer zone 104. The heat from the combustion of the combustion streams is carried downstream to heat the reactor bed's heat storing and transferring material internal to the combustion heat transfer zone 104. This heat is sufficient to heat the heat storing and transferring material to a temperature for carrying out the desired pyrolysis reaction according to the present techniques. The heat along with an oxidant (e.g., air not utilized in the combustion) may also be sufficient to remove or burn out carbon material that may be internal to the channels of flow in the combustion heat transfer zone 104. Preferably, combustion heat transfer zone 104 is comprised of separate channels, such as honeycomb channels, similar to that in first preheat zone 102. In one embodiment, the combustion heat transfer zone 102 may include a portion of a second reactor bed downstream of the reaction zone 103 and upstream of second reactor end zone 105, which may include removal components.

To enhance this system 100, a flushing fluid 119 may be added to the combustion products in the second reactor end zone 105. As noted above, the flushing fluid may include steam, which may be utilized to remove soot or coke from removal components or from pyrolysis injection components. In particular, the flushing fluid 119 may be utilized to remove coke or other deposits from injection and removal components (e.g., poppet valves), which may be exposed to the interior region of the reactor 100.

FIG. 2 shows an example of the pyrolysis step that is carried out according to an embodiment of the present techniques. For simplicity, certain reference numerals may be similar to designate similar portions of the reactor 100, as noted in FIG. 1. In FIG. 2, a pyrolysis feed 210 (e.g., hydrocarbons and optional fluids, such as molecular hydrogen ($H_2$)) is passed through the second reactor end zone 105 and passed to a pyrolysis preheat zone 202 of the pyrolysis reactor 100. As the hydrocarbon stream flows through the pyrolysis preheat zone 202, the hydrocarbon stream is heated and pyrolysis may begin to take place in a reactor zone 203. The reactor product, which includes reacted and unreacted hydrocarbons from the feed, continues downstream through the mixing components, if any, where the pyrolysis reaction continues. Undesirable by-products may be produced during the pyrolysis reaction, as the fluid flows from the pyrolysis preheat zone 202, through the reaction zone 203, and through the quenching zone 204. These undesirable by-products include compositions, such as coke or tar-like substances, and these substances can deposit within the pyrolysis reactor 100. A substantial portion of the coke or tar-like substances that may become deposited within the different zone can be removed during the regeneration mode.

Then, the reactor product is passed through the quenching zone 204 and continues to flow downstream toward and into the first reactor end zone 101. The reactor product 212 including the pyrolyzed hydrocarbons emerges from the first reactor end zone 101 into a product outlet or recovery step. A relatively small amount (e.g., around 1 wt % or less) of the coke or tar-like by-product that is produced during the pyrolysis reaction emerges from the first reactor end zone 101 along with the pyrolyzed hydrocarbons in the reactor product, which has an average temperature in the range of from 200° C. to 600° C., preferably in the range of from 300° C. to 500° C. Flushing fluid is injected into the first reactor end zone 101 to mix with the coke by-product as the reactor product flows downstream. Removal of the reactor product and flushing fluid from the first reactor end zone 101 of the pyrolysis reactor 100 is controlled by removal components, such as valves (not shown). The flushing fluid aids in removing the coke by-product out of the first reactor end zone 101. Coke build-up, therefore, is substantially reduced within the first reactor end zone 101, but also within or on the valves that are used to control the exit of the fluid stream.

The use of the flushing fluid 219 may enhance operation of the system by removing contaminates from the valves and other equipment, which provide gaseous seals between steps in the cycle. For instance, the system 100 may operate at cycle times in the range of 1 second to 60 seconds, in the range of 2 seconds to 20 seconds, or even in the range of 3 seconds to 10 seconds. With these rapid changes between steps, the removal of coke or other materials from within the reactor further enhances the operation of the system.

FIG. 3 is a diagram of an exemplary embodiment of a pyrolysis reactor 300 in accordance with an exemplary embodiment of the present techniques. According to FIG. 3, the regenerative reverse-flow reactor 300 includes a first reactor bed 302, a second reactor bed 304, one or more mixing components 306, insulation 307, one or more valves 308, head covers 309, one or more manifolds 310, fuel line 312, flushing fluid line 314, oxidant line 316, pyrolysis feed line 318, combustion removal line 320 and pyrolysis removal line 322. These components are utilized to manage the flow of the combustion streams, combustion products, pyrolysis stream, and reactor products through the reactor 300.

To operate the heating step, the combustion streams are provided to the reactor 300. The oxidant stream is provided via oxidant line 316, which passes through the corresponding open valves 308 and manifold 310 (e.g., poppet valves and associated manifolds). The fuel stream is provided via the fuel line 312, which includes fuel nozzles (not shown). In this configuration, the combustion streams flow through different channels in the first reactor bed 302, which is a honeycomb monolith. The combustion streams flow to the mixing components 306 disposed between the first reactor bed 302 and the second reactor bed 304. The mixing components 306 may be static mixers or baffles, which are configured to intermingle the fuel stream and the oxidant stream. The combustion products are passed through the second reactor bed 304 (e.g., a honeycomb monolith, which maybe similar to the first reactor bed 302), corresponding open valves 308 and manifolds 310 to the combustion removal lines 320. While in this heating step, the pyrolysis feed valves 308 remain closed to seal the associated manifold from the combustion streams and products.

Once the combustion products are removed, the pyrolysis step involves providing pyrolysis feed via pyrolysis feed line 318 to the region of the reactor 300. The hydrocarbon stream flows through different channels in the second reactor bed 304 and then to the mixing components 306. While flowing through these components, the hydrocarbons in the stream are heated to produce the reactor products. Then, the reactor products are passed through the first reactor bed 302, corresponding open valves 308 and manifolds 310 to the pyrolysis removal lines 322. While in this pyrolysis step, the combustion stream valves 308 remain closed to seal the associated manifold from the pyrolysis streams and products.

To enhance the operation of this reactor 300, the flushing fluid may be provided via the flushing fluid line 314 that is disposed between portions of the first reactor bed 302. The flushing fluid line 314 may include one or more injection components (e.g., nozzles or orifices) distributed along the flushing fluid line 314 to distribute the flushing fluid evenly through the end portion of the first reactor bed 304. The location of the flushing fluid line may be based on the upstream location from the region that coke is deposited within the reactor 300 (e.g., the valve 308 heads that are exposed to the interior of the reactor 300, end portion of the first reactor bed 302 that is adjacent to the pyrolysis removal components (e.g., valves 308 and manifolds 310 associated with the pyrolysis removal line 322), and/or the head cover 309 at this end of the reactor 300).

In other embodiments, which are not shown, the flushing fluid line 314 may be positioned in other locations. For instance, the flushing fluid line 314 may be disposed between the valves 308 and the first reactor bed 302. The location of the positioning of the flushing fluid line 314 may be at a location where the gas temperature is at or above the temperature where the reactions of acetylene to carbon have substantially slowed (at the relevant residence times (<0.1 s). This gas temperature may be measured by a thermocouple, as is known in the art. The gas temperatures that the flushing fluid may be introduced at are temperatures ≥200° C., ≥300° C., ≥400° C., or even ≥500° C. Further, the flushing fluid line 314 may be disposed at a location having a pyrolysis gas temperature ≤900° C., ≤800° C., ≤750° C. or ≤600° C. This location may further limit the exposure of the flushing fluid line to higher temperatures, prolong equipment usage, and minimize coking the flushing fluid lines 314.

For instance, the reactor 300 may include a flushing fluid line at each end of the reactor 300 or in only one end of the reactor 300. The location may include a flushing fluid line 314 disposed in the second reactor bed 304, which may be utilized to mix the flushing fluid with the combustion products (e.g., carbon dioxide) to clean a portion of the second reactor bed 304, the head cover 309, valves 308 and manifolds 310 adjacent to the second reactor bed. In another embodiment, the flushing fluid line may be disposed adjacent to one or both of the reactor beds. Also, the flushing fluid line may be shared with the fuel line 312 to provide the flushing fluid during a portion of the pyrolysis step, and the fuel line providing the fuel stream during the heating step.

Further, in other configurations, the flushing fluid lines may involve different configurations to distribute the flushing fluid. For example, the nozzles of the flushing fluid line 314 may be configured to provide a specific spray pattern within the reactor 300 or may be configured to spray specific components within the reactor. For example, the spray nozzles may be oriented to direct the flushing fluid toward valves 308. In addition, the flushing fluid line 314 may be a network of conduits or tubes and nozzles coupled together to distribute the flushing fluid to all or portions of the reactor 300. As an example, the flushing fluid line 314 may be disposed along the outer portion of the reactor 300 with the nozzles directed toward the center of the reactor 300. This configuration may utilize the flow of the products to distribute the flushing fluid, while minimizing the obstruction to the flow path of the streams flowing through the reactor 300. That is, the flushing fluid line 314 may be a circular tube around the perimeter of the internal surface of a circular shaped reactor interior or may include different line segments coupled together along the perimeter to form a rectangle for a rectangular shaped reactor interior. In another embodiment, the flushing fluid may include a network of lines coupled together to form a mesh to distribute the flushing fluid in a uniform manner. While this configuration may hinder streams through the reactor, the network may provide enhanced distribution of the flushing fluid and/or may distribute the flushing fluid to specific components.

Moreover, as noted above, the flushing fluid may be utilized at different steps of the process. As noted above, the flushing fluid may be provided as a separate step between heating and pyrolysis steps. Alternatively, the flushing fluid may be provided during a portion of the pyrolysis step and/or a portion of the heating step. In particular, the flushing fluid may be provided during the entire step, during the later half of the respective step, during the later quarter of the respective steps. Also, the flushing fluid may be provided for a predetermined period based on the composition of the pyrolysis feed, composition of the hydrocarbon feed, estimated coke production.

The flushing fluid may be managed by adjusting the period of supply or the amount of flushing fluid provided to the reactor 300. That is, a process control unit may be utilized to adjust the period or flow of flushing fluid based on a measured temperature or pressure changes in the operation of the reactor. The process control unit, which may be a computer system, may include a set of instructions stored in memory and executed by a processor to perform certain operations. The process control unit may be configured to receive measurement data from a pressure or temperature sensor that communicates measurement data to process control unit; compare the measurement data with stored operation parameters and calculate an adjustment to the flow of the flushing fluid or the period that the flushing fluid is provided; communicate the adjustment to a control unit. The control unit may include a flow control unit coupled to a flow valve for the flushing fluid coupled to the flushing fluid line (e.g., flushing fluid line 314). The pressure or temperature sensor may be disposed within the end of the reactor near the valves 308 and configured to monitor the temperature or pressure within the reactor 300.

Certain aspects of the invention are further specified in the following embodiments:

E1. A pyrolysis process, comprising: heating a stream in a preheat zone of a regenerative pyrolysis reactor; reacting the stream in a reaction zone of the pyrolysis reactor to produce a product; injecting a flushing fluid into the pyrolysis reactor to mix with the product downstream of the reaction zone; and removing the product from the pyrolysis reactor.

E2. The process of embodiment E1, wherein the flushing fluid is comprised of a polar fluid.

E3. The process of embodiment E1, wherein the flushing fluid is comprised of steam or a polar aprotic fluid.

E4. The process of embodiment E1, comprising quenching the product in a quenching zone upstream of the injecting, which may include the product comprising acetylene.

E5. The process of embodiment E3, wherein the injecting step is performed in a quenching zone upstream of the removing step.

E6. The process of any one of embodiments E4 and E5, wherein the injecting step is performed at a location within the regenerative pyrolysis reactor exposed to gas temperatures ≤900° C.

E7. The process of any one of embodiments E4 and E5, wherein the injecting step is performed at a location within the regenerative pyrolysis reactor exposed to gas temperatures ≤600° C.

E8. The process of embodiment E1, comprising transferring heat to a material in a heat transfer zone downstream of the reaction zone and upstream of the injecting, wherein the product comprises carbon dioxide.

E9. The process of embodiment E8, comprising:
heating a hydrocarbon stream in a second preheat zone of the regenerative pyrolysis reactor to produce a heated hydrocarbon stream; reacting the heated hydrocarbon stream in the reaction zone to produce a reactor product; quenching the reactor product in a quenching zone; mixing a second flushing fluid with the quenched reactor product; and removing the product from the pyrolysis reactor.

E10. The process of embodiment E1, comprising: separating the flushing fluid from the product downstream of the regenerative reactor; and recycling the separated flushing fluid to the reactor.

E11. The process of embodiment E1, wherein the stream is comprised of a hydrocarbon having a nominal end boiling point of at least 400° F. (204° C.).

E12. The process of embodiment E1, wherein the flushing fluid is injected into the reactor at a weight ratio of flushing fluid to the produced product exiting the reaction zone of at least 0.01:1.

E13. A system for processing hydrocarbons comprising: a regenerative pyrolysis reactor comprising: one or more injection components at a first end; a reaction zone downstream of the one or more injection components; one or more removal components at a second end downstream of the reaction zone; and a flushing fluid line downstream of the reaction zone and upstream of the one or more removal components configured to inject flushing fluid at a reactor product exit location downstream of the reaction zone.

E14. The system of embodiment E13, wherein the regenerative reactor comprises a first reactor bed and a second reactor bed coupled in series and disposed between the one or more injection components and the one or more removal components, wherein the reaction zone comprises a portion of at least one of the first reactor bed and the second reactor bed.

E15. The system of embodiment E14, wherein the regenerative reactor comprises one or more mixing components disposed between the first reactor bed and the second reactor bed and configured to intermingle streams within the reaction zone.

E16. The system of any one of embodiments E13 to E15, comprising a separator vessel downstream of the regenerative reactor and configured to separate the flushing fluid from a reactor product.

E17. The system of embodiment E16, comprising a water quench tower downstream of the separator vessel and configured to contact reactor product with a water quench fluid to further cool reactor product.

E18. The system of any one of embodiments E16 to E17, comprising a transfer line exchanger downstream of the regenerative reactor and upstream of the separator vessel and configured to cool the reactor product.

E19. The system of any one of embodiments E16 to E17, comprising one or more lines configured to recycle the flushing fluid from the separator vessel to the regenerative reactor.

E20. The system of any one of embodiments E13 to E19, wherein the flushing fluid line comprises a plurality of nozzles.

E21. The system of embodiment E20, wherein the plurality of nozzles is configured to distribute the flushing fluid to one or more removal components.

E22. The system of any one of embodiments E20 to E21, wherein the flushing fluid line comprises one or more lines disposed along an outer portion of an interior region of the regenerative reactor.

E23. The system of any one of embodiments E20 to E21, wherein the flushing fluid line comprises one or more lines of lines coupled together to form a mesh to distribute the flushing fluid to one or more removal components.

E24. The system of embodiment E14, wherein the flushing fluid line is disposed within the second reactor bed.

E25. The system of embodiment E14, wherein the flushing fluid line is disposed adjacent to the second reactor bed.

E26. The system of embodiment E13, comprising a second flushing fluid line upstream of the reaction zone and downstream of the one or more injection components.

E27. The system of embodiment E13, wherein the regenerative reactor comprises: one or more removal components at the first end; one or more injection components at the second end; and a second flushing fluid line downstream of the reaction zone and upstream of the one or more removal components.

The principles and modes of operation of the present techniques have been described above with reference to various exemplary and preferred embodiments. As understood by those of skill in the art, the overall invention, as defined by the claims, encompasses other preferred embodiments not specifically enumerated herein.

The invention claimed is:

1. A pyrolysis process, comprising:
heating a stream in a preheat zone of a regenerative pyrolysis reactor operating in a first flow direction, the regenerative pyrolysis reactor further comprising a pyrolysis reaction zone, a quenching zone, and at least one injection component, wherein the (i) the pyrolysis reaction zone is located downstream of the preheat zone, (ii) the quenching zone is located downstream of the pyrolysis reaction zone, (iii) the injection component is located downstream of the pyrolysis reaction zone, and (iv) upstream and downstream are indicated with respect to the first flow direction;
pyrolysing the stream in the pyrolysis reaction zone to produce a pyrolysis product, the product being quenched in the quenching zone;
injecting a hydrocarbon flushing fluid through the injection component into the regenerative pyrolysis reactor to mix with the product, wherein the flushing fluid comprises hydrocarbon; and
removing the product from the pyrolysis reactor.

2. The process of claim 1, wherein the flushing fluid is comprised of a polar fluid.

3. The process of claim 1, wherein the flushing fluid is comprised of steam or a polar aprotic fluid.

4. The process of claim 1, wherein the injection component is located in the quenching zone upstream of the removal of the product from the pyrolysis reactor.

5. The process of claim 1, wherein the injection of the flushing fluid is performed at a location within the regenerative pyrolysis reactor exposed to gas temperatures ≤900° C.

6. The process of claim 1, wherein the injection of the flushing fluid is performed at a location within the regenerative pyrolysis reactor exposed to gas temperatures ≤600° C.

7. The process of claim 1, further comprising switching the regenerative pyrolysis reactor from the pyrolysis step to a heating step, and transferring heat to the heat transfer zone and producing a second product which comprises carbon dioxide, wherein the heating step is carried out in a second flow direction that is substantially the reverse of the first flow direction.

8. The process of claim 1, comprising:
separating the flushing fluid from the product downstream of the regenerative pyrolysis reactor;
and recycling the separated flushing fluid to the reactor.

9. The process of claim 1, wherein the stream is comprised of a hydrocarbon having a nominal end boiling point of at least 400° F. (204° C.).

10. The process of claim 1, wherein the flushing fluid is injected into the regenerative pyrolysis reactor at a weight ratio of flushing fluid to the produced product exiting the reaction zone of at least 0.01:1.

* * * * *